United States Patent [19]

Duff

[11] Patent Number: 4,940,786

[45] Date of Patent: Jul. 10, 1990

[54] ONE-POT PREPARATION OF BISMUTH (PHOSPH/SULF)ATED SACCHARIDES

[75] Inventor: Steven R. Duff, DeSoto, Kans.

[73] Assignee: Marion Laboratories, Inc., Kansas City, Mo.

[21] Appl. No.: 429,460

[22] Filed: Oct. 31, 1989

[51] Int. Cl.$^5$ ............... C07H 11/00; C07H 13/00; C07H 23/00; C07H 1/00

[52] U.S. Cl. ................... 536/117; 536/17.1; 536/121; 536/118; 536/124; 536/122

[58] Field of Search .............. 536/117, 17.1, 121, 536/124, 118, 122

[56] References Cited

U.S. PATENT DOCUMENTS 3,379,717  4/1968  Koopman et al. ............ 536/18.1
3,432,489  3/1969  Nitta et al. .................. 536/118

FOREIGN PATENT DOCUMENTS 0230023  7/1987  European Pat. Off. .

OTHER PUBLICATIONS

Carey et al., *Advanced Organic Chemistry, Part B: Reactions and Synthesis,* Plenum Press (1977), pp. 482–496 & 507.

Andersen et al. (Eds.), *Chem. Sources U.S.A.,* Directories Publishing Co., Inc., Ormond Beach, Fl. (1984), pp. 158, 257, 259, 262, 311, 326, 447 & 467.

*Primary Examiner*—Ronald W. Griffin
*Assistant Examiner*—Everett White
*Attorney, Agent, or Firm*—Christopher John Rudy

[57] ABSTRACT

Bismuth salts of phosphorylated and/or sulfonated saccharides can be prepared in one reaction vessel from a corresponding metal salt reactant, a water soluble organic acid, and a bismuth substance. For example, a complex salt of bismuth hydroxide sucrose octasulfate can be prepared in high yield and good purity from potassium sucrose octasulfate, trifluoracetic acid, and bismuth hydroxide.

9 Claims, No Drawings

4,940,786

ONE-POT PREPARATION OF BISMUTH (PHOSPH/SULF)ATED SACCHARIDES

FIELD

This invention especially concerns preparation of bismuth phosphorylated and/or sulfonated saccharides. These saccharides are generally useful as pharmaceuticals or intermediates thereto.

BACKGROUND

Bowen et al., U.S. patent application Ser. No. 07/209,372 filed on Jun. 21, 1988, U.S. Pat. No. 4,918,175 (Apr. 17, 1990), discloses bismuth (phosph/sulf)ated saccharides. In nature and gist, these compositions are bismuth phosphorylated and/or sulfonated saccharides, which are useful as pharmaceuticals in ameliorating disorders associated with gastric mucosal damage. Preparation of the bismuth (phosph/sulf)ated saccharides according to the practice of that invention involves contacting a hydrogen (phosph/sulf)ated saccharide with a bismuth substance. Preparations from metal salts of the (phosph/sulf)ated saccharides, other than bismuth of course, involve, for example, ion exchange procedures with an ion exchange resin such as a sulfonated divinyl benzene in its hydrogen ion form. The metal salt, for example, the potassium salt, is passed over the resin to prepare the hydrogen (phosph/sulf)ated saccharides, which are used for contacting with the bismuth substance, for example, freshly prepared bismuth hydroxide, to prepare the bismuth (phosph/sulf)ated saccharides.

Duff, U.S. patent application Ser. No. 07/351,714 filed on May 15, 1989, abandoned in favor of Ser. No. 07/430,059 filed on Oct. 31, 1989, discloses preparation of hydrogen and bismuth (phosph/sulf)ated saccharides. In summary, that invention, in one aspect, provides a process for preparing a hydrogen (phosph/sulf)ated saccharide comprising contacting a metal salt of a (phosph/sulf)ated saccharide with a water soluble organic acid having a pKa less than the pKa of the hydrogen (phosph/sulf)ated saccharide to be prepared, by steps under conditions such that the hydrogen (phosph/sulf)ated saccharide is prepared. Another aspect provides a process for preparing a bismuth (phosph/sulf)ated saccharide comprising steps of contacting, first, a metal salt of a (phosph-sulf)ated saccharide with a water soluble organic acid having a pKa less than the pKa of a hydrogen (phosph/sulf)ated corresponding to the bismuth (phosph/sulf)ated saccharide to be prepared, and second, the product of said first step with a bismuth substance, by steps under conditions such that the bismuth (phosph/sulf)ated saccharide is prepared.

What is lacking and needed is a process which can prepare hydrogen and/or bismuth (phosph/sulf)ated saccharides, particularly from salts other than of course bismuth, that is simpler and more efficient than, heretofore known. Desirably, the process would be employable with advantage in preparation of large or commercial scale amounts of the product (phosph/sulf)ated saccharide.

SUMMARY

This invention provides a process for preparing a bismuth (phosph/sulf)ated saccharide comprising steps of, first, contacting a component of a metal salt of a (phosph/sulf)ated saccharide with components of a bismuth substance and a water soluble organic acid having a pKa less than the pKa of a hydrogen (phosph/sulf)ated saccharide generally corresponding to the bismuth (phosph/sulf)ated saccharide to be prepared, and second, maintaining contact of said components in mixture provided by said first step, under conditions such that the bismuth (phosph/sulf)ated saccharide is prepared.

This invention prepares useful pharmaceutical products.

This invention fulfils the aforementioned lacks and needs in the art. Advantageously, this invention can be employed in highly efficient preparation of large or commercial scale amounts of the desired bismuth (phosph/sulf)ated saccharide(s) suitable as is as a pharmaceutically employable component. Notably, the practice of this invention can be carried out in one reaction vessel or pot, and amounts of the organic acid used can be conservatively low.

Further significant advantages attend this invention.

ILLUSTRATIVE DETAIL

In general, the bismuth (phosph/sulf)ated saccharides prepared by the practice of this invention are those found from the practice of the aforementioned Bowen et al. and Duff invention, which thus contain such a component as bismuth. These (phosph/sulf)ated saccharides further contain such a component as a phosphorylated and/or a sulfonated saccharide, which is a saccharide generally having more than one moiety selected from such moieties as at least one of phosphate and sulfate moieties esterified thereto.

The component such as a sulfate ester and/or a phosphate ester saccharide includes thus such saccharides as (1) sulfated saccharides, (2) phosphated saccharides, (3) sulfated-phosphated saccharides, and (4) mixtures thereof. Saccharide components having at least three sulfate ester moieties per saccharide nucleus are desirably employed. Polysulfated saccharides are more typically employed in the practice of this invention. The polysulfated saccharides desirably contain substantial amounts of persulfated saccharides.

Saccharide moieties themselves which may be employed in the practice of this invention include mono-, di-, tri-, tetra- and oligosaccharides. Examples of suitable saccharide nuclei or moieties may be selected from appropriate residues of such saccharides as erythrose, threose, arabinose, deoxyribose, fructose, glucose, ribose, mannose, lactose, cellobiose, maltose, sucrose, trehalose, melezitose, stachyose, and so forth and the like. The saccharide moieties desirably are disaccharides of pentoses and/or hexoses. Sucrose is preferred.

In general, the bismuth (phosph/sulf)ated saccharides contain the component such as bismuth. The component such as bismuth includes such metallic elements as bismuth, and especially in the final pharmaceutical product. pharmaceutically acceptable compounds therewith.

Pharmaceutically acceptable compounds with bismuth include, of course, molecular level covalent or ionic complexes with bismuth and the phosphated and/or sulfated saccharide moieties, molecular level covalent or ionic complexes with such bismuth-containing moieties or compounds as bismuth hydroxides and the phosphated and/or sulfated saccharide moieties, these compositions in the presence of a suitable pharmaceutical carrier, and so forth and the like.

The bismuth (phosph/sulf)ated saccharides may be a composite mixture, i.e., a composition combining more than one chemical entity to make up the composition. They may be considered complex bismuth salts of (phosph/sulf)ated saccharide(s). A water of hydration is desirably present.

The bismuth (phosph/sulf)ated saccharides are generally insoluble in water, lower alcohols, e.g., methanol, lower ketones, e.g., acetone, dilute aqueous hydrochloric acid, for example, 0.1N HCl(aq), with generally no gelling propensity in acidic water.

In general, the metal salts of the (phosph/sulf)ated saccharide employed in the practice of this invention are saccharides analogous to hydrogen (phosph/sulf)ated saccharides but having metal ions generally replacing the hydrogen ions from phosphoric and sulfonic moieties of the hydrogen (phosph/sulf)ated saccharides, and of course, in general, these hydrogen (phosph/sulf)ated saccharides are saccharides analogous to those of the corresponding bismuth (phosph/sulf)ated saccharides, but having phosphoric and sulfonic acid moieties bonded therewith, with sulfonic acid moieties being preferred. Suitable metals in this connection include alkali and alkaline earth metals, especially the alkali metals. Potassium salts are preferred.

Desired metal salts of the (phosph/sulf)ated saccharides are those being generally soluble in water and such hydroxylated organic compounds as methanol, ethanol, propanols, and so forth, also being substantially soluble in those diluents in which the corresponding bismuth (phosph/sulf)ated saccharides are substantially insoluble. Advantageously, such a diluent is one as, for example, water.

Phosphorylation and/or sulfonation may be accomplished on corresponding saccharides having appropriate esterfication site(s) available, as is known in the art. For example, phosphorylation may be accomplished by appropriate treatment of a hydrogen saccharide with a suitable phosphorylating agent, for example, one which may be phosphoryl chloride or cyanoethyl phosphate. See e.g., Carey et al., *Advanced Organic Chemistry, Part B: Reactions and Synthesis*, Plenum Press, New York (1977), at pages 482–96 & 507. Sulfonation may be accomplished by appropriate treatment of a hydrogen saccharide with a suitable sulfating agent, for example, chlorosulfonic acid, anhydrous sulfuric acid or sulfur trixode-pyridine complex in a solvent such as pyridine, formamide, dimethyl formamide, chloroform or liquid sulfur dioxide. See e.g., Nitta et al., U.S. Pat. No. 3432489. See also, for example, Michaeli, EP 0230023, especially for preparations with and illustrations of sodium and potassium sulfate saccharides. Such phosphorylation and/or sulfonation can be used at the end of the first major phase of the aforementioned Duff invention with incompletely phosphorylated or sulfated saccharides to prepare more highly phosphorylated or sulfated saccharides, to include mixed varieties thereof. Alternatively, known hydrogen (phosph/sulf)ated saccharides can be phosphorylated and/or sulfonated. Various hydrogen (phosph/sulf)ated saccharides are known. See e.g., Andersen et al. (Eds.), *Chem Sources U.S.A.*, Directories Publishing Co., Inc., Ormond Beach, Fla. (1984), pages 158, 257, 259, 262, 311, 326, 447 & 467, for some examples of those commercially available. Such hydrogen (phosph/sulf)ated saccharides can be converted into a metal salt of the (phosph/sulf)ated saccharide for use as a reactant in the process of the present invention.

Thus, the metal salts of the (phosph/sulf)ated saccharides employed in the practice of the invention are known, or they can be prepared by such methods as those aforementioned or methods analogous thereto. Many of the metal salts of the (phosph/sulf)ated saccharides employed in the practice of this invention can be obtained commercially.

In general, the water soluble organic acid having a pKa less than the pKa of a hydrogen (phosph/sulf)ated saccharide which corresponds to the bismuth (phosph/sulf)ated saccharide to be prepared has the following characteristics among others. It is generally, advantageously—substantially, and preferably—completely, soluble in water or the reaction media in which it is employed in the practice of this invention. It is an organic acid, i.e., an acid bearing organic carbon, as this is known in the art. It has a pKa less than the pKa of a hydrogen (phosph/sulf)ated saccharide appropriately corresponding to the bismuth (phosph/sulf)ated saccharide to be prepared, generally exclusive of derivatization, for example, derivatization to the saccharide moieties or nuclei, or residues thereof, which can be carried out in the practice of this invention subsequent to preparation of the bismuth (phosph/sulf)ated saccharide which correspond to such a hydrogen (phosph/sulf)ated saccharide. As an illustrative example, an aqueous solution of hydrogen sucrose octasulfate, commonly known as sucrose octasulfate, has a pKa of about 1.33. Accordingly, the organic acid used in the practice of this invention to prepare the hydrogen sucrose octasulfate or bismuth sucrose octasulfate will have a pKa of less than about 1.33, to include for example, a pKa of about 1.30 or less. Preferably, the water soluble organic acid used in the practice of this invention is selected from among appropriate carboxylic or sulfonic acids. Suitable illustrative examples thus include trichloroacetic acid, trifluoroacetic acid and 4-methylbenzenesulfonic acid, and so forth and the like. Desirably, the organic acid used in the practice of this invention is trifluoroacetic acid.

In general, the bismuth substance contains bismuth, which, when employed in the practice of this invention, can form the bismuth (phosph/sulf)ated saccharide. As an illustration, the bismuth substance may be bismuth hydroxide (bismuth trihydroxide). Freshly prepared bismuth hydroxide is preferred. Commercially available bismuth hydroxide may contain other bismuth species such as bismuth carbonate and/or bismuth oxides, and so forth, and may not work as well as the freshly prepared bismuth hydroxide in the practice of this invention.

In the practice of this invention, first, a component of a metal salt of a (phosph/sulf)ated saccharide is contacted with components of a bismuth substance and a water soluble organic acid having a pKa less than the pKa of a hydrogen (phosph/sulf)ated saccharide generally corresponding to the bismuth (phosph/sulf)ated saccharide to be prepared, and second, contact of said components in the mixture provided by said first step is maintained. Conditions are those sufficient to prepare the desired product.

In general, amounts of the water soluble organic acid employed in the practice of this invention are those suitable to obtain the desired product. Typically however, in terms of molar equivalents of phosphorylated and/or sulfated moieties on the saccharide nuclei of the (phosph/sulf)ated saccharide moieties of the metal salt of the (phosph/sulf)ated saccharide reactant employed, in comparison to molar equivalents of acid with the water soluble organic acid employed, molar equivalent amounts of organic acid equivalents are about from a slightly less than stoichiometric amount to a slightly moderate excess amount in comparison to molar equivalent amounts of the phosphorylated and/or sulfated moieties on the saccharide moieties provided with reactant metal salt, for advantageous production. Of course, if significantly less amounts of the water soluble acid are employed, incomplete conversion of the entire metal salt reactant sample to desired product may result. The slightly moderate excess amount includes molar equivalent amounts of acid of the water soluble organic acid of about one and one half times as many as molar equivalent amounts of phosphorylated and/or sulfated moieties on the (phosph/sulf)ated saccharide residues of the metal salt reactant sample employed. In terms of ratios of acid equivalents to phosphorylated and/or sulfated moiety equivalents, ratios of about from 0.8:1 to 1:2 are included as generally and suitable, with the typical of such ratios being about from 0.9:1 to 1:1.5, and with preferred ratios being about from 0.9:1 to 1:1.2. In terms of more typically employed metal salt reactants having polysulfated saccharide moieties, and of course, poly(phosph/sulf)ated saccharide moieties as well, a molar excess of the water soluble organic acid is typically employed in relation to number of molar equivalents of metal salt of the (phosph/sulf)ated saccharide containing such poly(sulfated and/or phosphorylated) saccharide moieties. The excess referred to is typically a moderately substantial excess of the water soluble organic acid employed in the practice of this invention. This excess includes a molar excess of the organic acid at least about three times the number of moles of the reactant metal salt(s) of the (phosph/sulf)ated saccharide(s). Typically, the excess resides within a range of about from a fivefold to a tenfold molar excess of the organic acid compared to the reactant metal salt(s). Preferably, the excess resides within a range about from a sevenfold to a ninefold molar excess of the organic acid thus compared. Most preferably, the excess is an about 8.1 molar equivalent excess of trifluoroacetic acid.

Reaction media are typically aqueous, although other suitable media may be employed with water or apart therefrom to include, for example, methanol, ethanol, and so forth and the like. Water itself is advantageously employed in the preferred practice of this invention.

The reactant metal salt is generally dispersed at a suitable concentration in the reaction medium chosen. Initial concentrations of the reactant metal salt therein include those selected from the range about from 1 molar (M) to 0.0001M (0.1 mM). In preferred practice of this invention, reactant metal salt concentrations are in general initially about from 1 to 5 mM.

The bismuth substance and the water soluble organic acid are typically added to the dispersed reactant metal salt. The bismuth substance is preferably added thereto first. This is not required, but a better yield typically results from thus adding the bismuth substance first. Either or both of these components can be mixed with a suitable diluent before contact with any other component(s).

Typically, the bismuth substance is a solid, and it may advantageously be stirred into a dispersion or solution to make up its component of the reaction mixture. For example, the bismuth substance may be slurried in water as a sample of fine particles. Amounts of the bismuth substance employed may advantageously be in a slight stoichiometric molar equivalent deficeincy in comparison to the initial amount of phosphorylated or sulfated moiety equivalents of the reactant metal salt, to include, for instance, amounts about from 95 to 99.9 percent of theory, and for example, amounts about 99.4 percent of theory. However, amounts of bismuth up to about 105 percent of theory may be employed.

The initial contact of the components of the bismuth substance and the water soluble acid with the reactant metal salt component is carried out at a suitable temperature. Suitable temperatures include those selected about from 0 to 45 degrees C. Advantageously, the temperature at this contact is about from 15 to 30 degrees C., and preferably ambient room temperature.

At this point, the contact is maintained, with temperatures desirably being about the same as those employed in the initial contact step. Generally, the components are mixed at this step of the process. Duration of the step involving the maintaining of the contact of the components can be, say, from a score, i.e., twenty, minutes to a score of hours or more. Typically, this step is carried out for about from two to ten hours.

Upon completion of the desired progress of reaction, product bismuth (phosph/sulf)ated saccharide is generally separated from other components included in the remaining reaction mixture. This can be accomplished by known methodology. The recovery of the product advantageously can be carried out by suction filtration and washing. The washing may generally be with such liquids as, for example, water, methanol and/or acetone, and so forth and the like. The product can be slurried in methanol and/or acetone and suction filtered therefrom if desired.

The product can be dried after its collection. If it is desired that the product is to be dried, temperatures of the drying are advantageously moderate, but preferably any drying is carried out at ambient temperature under vacuum. Heating of the bismuth product to dry it should be avoided because such heating, as in air at temperatures much above usual ambient temperatures, for example, 45 degrees C. or more, may cause its decomposition. Accordingly, the product is advantageously stored under refrigeration, for example, in a refrigerator or freezer. Generally, cautionary protection from exposure to actinic radiation may be provided as with, for example, an amber or opaque glass bottle. Nonetheless, the bismuth product from the practice of this invention typically has diluent coordinated to it, e.g., water, and it is generally more stable if such a coordinated substance is left with the bismuth product molecule. Thus, any drying need not be, and desirably is not, carried out to a point where a product without coordinated substance, e.g., an anhydrous-type product, is prepared.

Therefore, desirable yields of the product can be exceedingly high, substantially quantitative, if not greater than quantitative when calculated on the basis of bismuth product without coordinated substance, e.g., water. Thus, such yields of at least about 100 percent of theory, to include yields of about from 100 to 120 percent of theory, are obtainable by the practice of this invention.

Purity of the product, particularly without additional purifications, can be excellent. Thus, for example, purity of the bismuth (phosph/sulf)ated saccharide product so obtained can be at least about 90 percent by weight, which is of an excellent pharmaceutical value for the bismuth (phosph/sulf)ated saccharide product.

The following example further illustrates this invention. Parts and percentages therein are by weight unless specified otherwise.

EXAMPLE

To a solution of potassium sucrose octasulfate (6.52 g, 5.06 mmol) in water (200 mL) was added freshly prepared bismuth hydroxide (10.47 g, 40.3 mmol, 7.95 molar equivalents), and then trifluoroacetic acid (4.67 g, 41.0 mmol, 8.1 molar equivalents) in water (10 mL) was added thereto. The mixture was stirred at room temperature for six hours. A solid was obtained and collected by suction filtration, washed with water and acetone and dried under vacuum at ambient temperature. Obtained was a complex hydrated salt of bismuth hydroxide sucrose octasulfate as a white solid (15.87 g, 107 percent of theory based on anhydrous product).

Elemental analysis, calculated for $C_{12} H_{30} O_{51} Bi_8 S_8$: C, 4.94; H, 1.04; S, 8.79; Bi, 57.28; K, 0.0; F, 0.0. Found: C, 4.64, 4.79; H, 1.78, 1.94; S, 8.19, 8.04; Bi, 52.33, 52.88; K, 0.51, 0.52; F, 0.0025, 0.0039.

Karl Fischer water analysis: 12.72, 12.81 percent

High pressure liquid chromotography analysis: Heptasulfate/octasulfate ratio: 0.0054; 32.32 percent sucrose octasulfate residue moiety in the product.

X-ray powder diffraction analysis: Bismuth hydroxide: None detectable.

CONCLUSION

The present invention is this provided. Various adaptations and modifications can be effected by those skilled in the art within the spirit of this invention, the scope of which is particularly pointed out by the following distinctly claimed subject matter.

What is claimed is:

1. A process for preparing a bismuth (phosph/sulf)ated saccharide comprising steps of, first, contacting a component of a metal salt of a (phosph/sulf)ated saccharide with components of a bismuth substance and a water soluble organic acid having a pKa less than the pKa of a hydrogen (phosph/sulf)ated saccharide generally corresponding to the bismuth (phosph/sulf)ated saccharide to be prepared, wherein, in said first step, the metal salt of a (phosph/sulf)ated saccharide is contacted first with the bismuth substance component, and then the mixture which results therefrom is contacted with said water soluble acid component, and second, maintaining contact of said components in the mixture provided by said first step, under conditions such that the bismuth (phosph/sulf)ated saccharide is prepared.

2. The process of claim 1, wherein yield of the bismuth (phosph/sulf)ated saccharide is at least about 100 percent of theory when calculated on the basis of bismuth product without coordinated substance.

3. The process of claim 1, which is conducted in an aqueous diluent.

4. The process of claim 3, wherein said metal salt is an alkali metal salt of a (phosph/sulf)ated saccharide, and said water soluble acid is selected from the group consisting of carboxylic acids and sulfonic acids.

5. The process of claim 4, wherein temperatures of said steps are about from 0 to 45 degrees C.

6. The process of claim 5, wherein (phosph/sulf)ated saccharide moieties are sulfonated, and the bismuth substance is bismuth hydroxide.

7. The process of claim 6, wherein said metal salt is potassium sucrose octasulfate; said water soluble organic acid is selected from the group consisting of trichloroacetic acid, trifluoroacetic acid and 4-methylbenzenesulfonic acid, and is employed in an amount about from seven to nine times as many moles as moles of said metal salt; temperatures of said steps are about from 15 to 30 degrees C., and a hydrated complex salt of bismuth hydroxide sucrose octasulfate is prepared in a yield of at least about 100 percent of theory based upon an otherwise anhydrous product at a purity of at least about 90 percent by weight.

8. A process for preparing a hydrated complex salt of bismuth hydroxide sucrose octasulfate comprising contacting an aqueous solution of potassium sucrose octasulfate with an aqueous mixture having about from 90 to 105 percent as many moles of bismuth hydroxide as there are moles of the potassium sucrose octasulfate, at a temperature about from 0 to 45 degrees C., to form a first mixture, then contacting said first mixture with about from seven to nine times as many moles of trifluoroacetic acid as there are moles of the potassium sucrose octasulfate, in an aqueous diluent at a temperature about from 0 to 45 degrees C., to form a second mixture, then maintaining contact of said second mixture for a time about from 20 minutes to 20 hours at a temperature about from 0 to 45 degrees C., and then separating the hydrated complex salt of bismuth hydroxide sucrose octasulfate from the aqueous reaction mixture.

9. The process of claim 8, wherein yield of the hydrated complex salt of bismuth hydroxide sucrose octasulfate is at least about 100 percent of theory when calculated on the basis of anhydrous bismuth product.

* * * * *